United States Patent [19]

Muntz et al.

[11] 4,067,932

[45] Jan. 10, 1978

[54] DERIVATIVES OF PHOSPHORUS-CONTAINING ALDEHYDES AND KETONES

[75] Inventors: Ronald L. Muntz, Bedford Hills; Edward N. Walsh, New City, both of N.Y.

[73] Assignee: Stauffer Chemical Company, Westport, Conn.

[21] Appl. No.: 692,158

[22] Filed: June 2, 1976

[51] Int. Cl.$^2$ .............................. C07F 9/09; C07F 9/40
[52] U.S. Cl. ............................... 260/927 R; 260/931; 260/932; 260/936; 260/937; 260/945; 260/946; 260/953; 260/968; 260/970
[58] Field of Search .................. 260/927 R, 931, 932, 260/936, 937, 945, 944, 953

[56] References Cited

U.S. PATENT DOCUMENTS

| | | | |
|---|---|---|---|
| 2,974,158 | 3/1961 | Lanham | 260/927 R |
| 3,076,010 | 1/1963 | Beck et al. | 260/945 |
| 3,158,640 | 11/1964 | Le Suer | 260/932 |
| 3,177,208 | 4/1965 | Stilz et al. | 260/932 X |
| 3,255,145 | 6/1966 | Graham | 260/932 X |
| 3,515,776 | 6/1970 | Baranauckas et al. | 260/927 R |
| 3,830,886 | 8/1974 | Davis et al. | 260/953 |
| 3,969,437 | 7/1976 | Shim | 260/937 |

*Primary Examiner*—Richard L. Raymond
*Attorney, Agent, or Firm*—William R. Robinson

[57] ABSTRACT

Phosphorous based flame retardants based on organophosphorus intermediates, characterized by high phosphorus content, which allow further reaction with conventional organophosphorus compounds are described. These flame retardants are particularly useful or polyurethanes.

2 Claims, No Drawings

DERIVATIVES OF PHOSPHORUS-CONTAINING ALDEHYDES AND KETONES

BACKGROUND OF THE INVENTION

1. Field of the Invention

The present invention relates to new and improved phosphorus containing flame retardants.

2. The Prior Art

The technology involved in flame retarding of rigid urethanes has progressed rapidly in the past twenty years. Despite many efforts to find new approaches to flame retard urethanes, however, those approaches requiring phosphorus and halogen compounds remain dominant.

Urethane flame retardants in today's marketplace must be low in cost and have high flame retarding efficiency. Also, they should not have an adverse effect on the urethane components, the resin forming process or the physical properties of the resulting foam.

Some relatively low cost reactive intermediates which can be readily converted to effective flame retardants, but have not received much notice in the past are phosphorus containing aldehydes and ketones. They are particularly effective, reactive intermediates that can be utilized to make flame retardants for polyurethanes.

SUMMARY OF THE INVENTION

The phosphorus containing aldehydes and ketones utilized as the reactive flame retardant intermediates of the present invention can be prepared by various well established chemical routes from readily available, low cost raw materials. Said aldehydes and ketones can undergo a wide variety of reactions. Accordingly, they open doors to numerous new phosphorus flame retardants, both non-reactive and reactive. Moreover, they provide routes to products containing high concentrations of phosphorus, in the range of about 10% to about 25%.

The derivatives of the phosphorus containing aldehydes and ketones have the general structural equation:

$$(RO)_2 P(O)_n R' \quad \text{I}$$

or

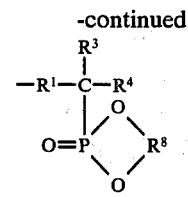

wherein $n$ is 1 or 0 and R' has the general structure: (1),(2) or (3)

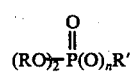

or

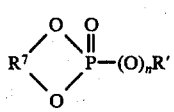

or

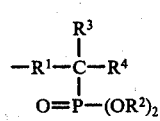

where R and $R^2$ are the same or different and are selected from the group consisting of $C_1$-$C_6$ straight, branched, or cyclic alkyl, aryl, aryl substituted $C_1$-$C_6$ alkyl, $C_1$-$C_6$ alkyl substituted aryl, and hydroxy containing derivatives thereof and $R^7$ and $R^8$ are the difunctional analogs of R and $R^2$. $R^1$ is selected from the group consisting of straight or branched $C_1$-$C_6$ alkylene or alkenylene; $R^3$ is selected from the group consisting of hydrogen, and $C_1$-$C_4$ straight or branched alkyl; $R^4$ is selected from the group consisting of hydroxyl, and $-N(R^9)_2$ wherein $R^9$ is $C_1$-$C_4$ alkyl and hydroxy alkyl; $R^5$ is selected from the group consisting of hydrogen and $C_1$-$C_6$ straight and branched alkyl; and $R^6$ is selected from the group consisting of $-C(CH_2-OH)_3$ and $-CH_2-CH[N(R^9)_2]_2$ wherein $R^9$ is the same as defined above.

The foregoing derivatives of phosphorus containing aldehydes and ketones will react into the urethane either in the polymer backbone or as a pendant group.

These derivatives can be prepared by addition or condensation reactions with the aldehyde or ketone group. The reactions are according to the following generalized reaction schemes:

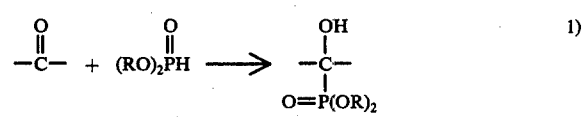

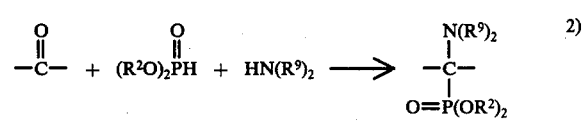

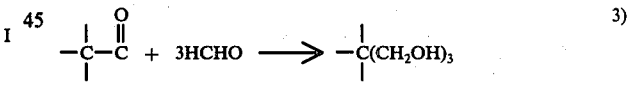

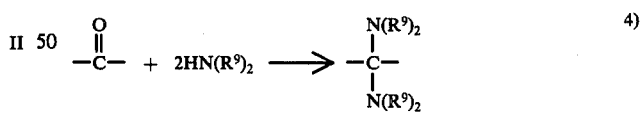

DETAILED DESCRIPTION OF THE INVENTION

Typical derivatives of phosphorus aldehydes and ketones utilized in the present invention are as follows:

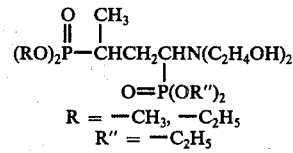

-continued

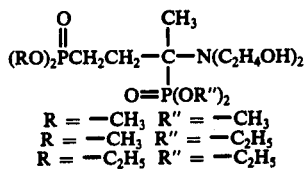

R = —CH₃, —C₂H₅
R" = —C₂H₅

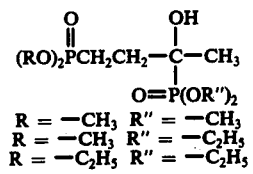

R = —CH₃  R" = —CH₃
R = —CH₃  R" = —C₂H₅
R = —C₂H₅  R" = —C₂H₅

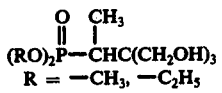

R = —CH₃  R" = —CH₃
R = —CH₃  R" = —C₂H₅
R = —C₂H₅  R" = —C₂H₅

(RO)₂P(O)—CHC(CH₂OH)₃
R = —CH₃, —C₂H₅

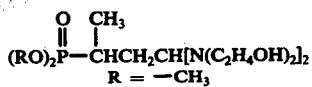
R = —CH₃

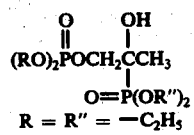
R = R" = —C₂H₅

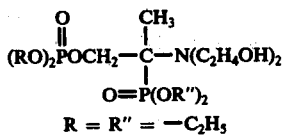
R = R" = —C₂H₅

Various established reaction routes can be used to synthesize the phosphorus containing aldehydes and ketones utilized in the present invention. Some of these are summarized as follows:

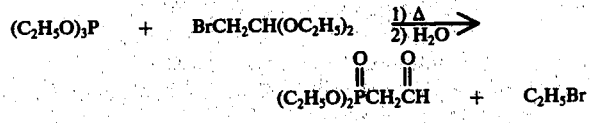

N. Dawson and A. Burger, J. Am. Chem. Soc., 74, 5312 (1952)

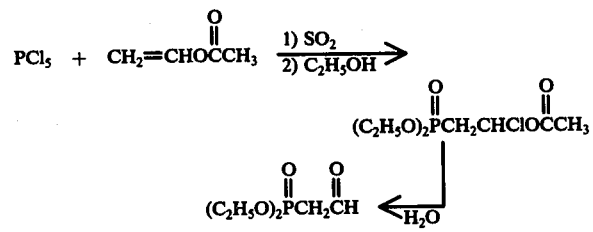

F. Lutsenyko and M. Kirilov, Doklady Akad. Nauk. SSSR, 132, 842 (1960)

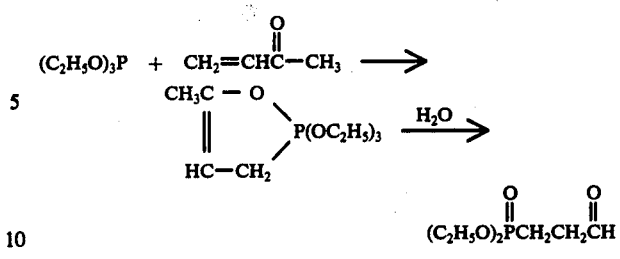

G. Kamai and V. A. Kukhtin, Doklady Akad Nauk SSSR, 112, 836 (1957) R. G. Harvey, Tetrahedron, 1966, 2561

K. Kraus, Compt. rend. C271, 74 (1970)

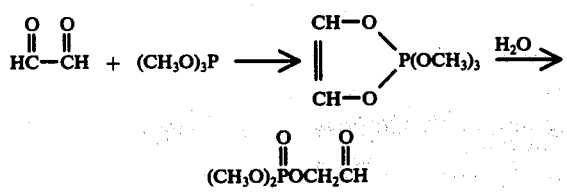

F. Ramirez et al., J. Am. Chem. Soc., 91,496 (1969) Additional discussion of reaction routes appears in *Russian Chemical Reviews*, 42 (7),538 (1973) by A. I. Razumov et al.

Addition or condensation reaction schemes with the phosphorus containing aldehydes and ketones of the present invention are utilized to prepare high phosphorus content derivatives. These derivatives can be incorporated into urethane either in the polymer backbone or as a pendant group.

Hydrogen phosphonate adducts are prepared by reaction of phosphorus aldehydes or ketones with a phosphite or phosphonate in the presence of a basic catalyst at a temperature from about 0° C. to about 120° C. The reaction can be carried out with or without a solvent. If a solvent is utilized, it can be selected from aromatic hydrocarbons, aliphatic hydrocarbons, alcohols or other non-reactive liquids. Any basic catalyst is suitable with stronger bases such as sodium, potassium and sodium hydride being utilized with the ketones. Weaker bases such as organic amines can be utilized as catalysts with the aldehydes.

Condensation products according to the present invention are prepared by condensing phosphorus containing aldehydes or ketones with a secondary amine and a hydrogen phosphonate at a temperature from about 20° C. to about 150° C. The condensation is carried out in a one or two step Mannich procedure and can be accomplished with or without a solvent or in the presence of an inert liquid. Typical inert liquids are hexane, toluene and chlorobenzene.

In the two step procedure an azeotroping solvent can be utilized. Aromatic hydrocarbons such as benzene or toluene are suitable.

The products of the present invention can be neutralized. Exemplary neutralizing agents are ethylene oxide and propylene oxide.

The addition and condensation products of the present invention are incorporated into urethane foams by standard procedures. This is typically done by premixing the flame retardant with the polyol. The alternate methods of prereacting the flame retardant with the isocyanate or mixing several components simultaneously, however, are feasible.

The present invention will be more fully illustrated in the examples which follow.

EXAMPLES

A. Preparation of phosphorus-containing aldehydes & ketones

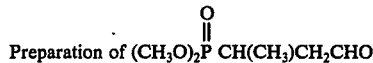

I.

A mixture of crotonaldehyde (400g) and methanol(400ml) was placed in a 2 liter 3-neck flask equipped with a thermometer, reflux condenser, addition funnel, magnetic stirrer, and ice water cooling bath.

To this mixture trimethyl phosphite (710g) was added dropwise over a 3 hour period giving a slight exotherm. The maximum pot temperature was 36° C. After standing 16 hours at room temperature the mixture was heated at reflux (80°-85° C.) for 8½ hours. Volatiles were then removed by vacuum stripping on a rotary evaporator.

Water (210g) was mixed with concentrated HCl (5ml) and added to the residue from the vacuum stripping. This was done in order to hydrolyze the intermediate acetal. This reaction mixture was allowed to stand 16 hours at room temperature, heated at 50°-60° C. for 2 hours and distilled. Distillation was carried out under gradually reduced pressure. The major product fraction contained 573g and boiled at 98°-117° C. at 0.07-0.30mm. The yield was 57%. The infra red spectra showed a strong carbonyl absorption at 1717cm$^{-1}$ and a strong phosphoryl absorption at 1240-1250cm.$^{-1}$ This preparation as well as II, III, & IV all use the method described by R. G. Harvey, *Tetrahedron*, 22, 2561-2573 (1966).

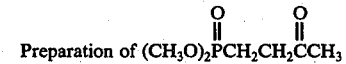

II.

The same apparatus and procedures were used as in part I. The reagents employed were methylvinylketone (400g), methanol (400ml), and trimethyl phosphite (708g). In this case the addition was carried out over a 2 hour period and the maximum pot temperature was 54° C. It was necessary to keep cooling the reaction mixture for an hour after the addition was complete.

Hydrolysis of the intermediate ketal was carried out by adding a mixture of concentrated HCl (5ml) and water (200ml) to the residue left after volatiles had been removed. The product was distilled at 106°-116° C. The yield was 700g (81%). Again the infra red spectra showed a strong phosphoryl absorption at 1250cm$^{-1}$ and a strong carbonyl absorption at 1716cm$^{-1}$.

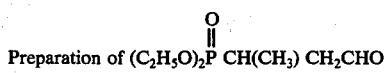

III.

The same equipment and procedure was used as in I. except a 1 liter reaction vessel was employed. The following reagents were used:
Ethanol-150g
Crotonaldehyde-100g
Triethyl phosphite-237g The phosphite addition was completed in 2½ hours. The maximum pot temperature was 52° C.

After stripping volatiles from the reaction mixture, 52ml of water plus 3 ml of concentrated HCl were added and the mixture was heated to 90° C. Volatiles were allowed to slowly distill at a head temperature on ca. 70° C. Finally aspirator vacuum was applied to complete removal of the volatiles (ca. 200ml).

The residue remaining after stripping was distilled. The major fraction (120g, 40% yield) distilled at 105°-117° C. and 0.4-0.5mm. The boiling point is 99° C. at 0.05mm.

IV.

This reaction was carried out as in I. except the following reagents were used:
Methylvinylketone-300g
Ethanol-600ml
Triethyl phosphite-712g The addition of phosphite was completed in 5 hours. The maximum pot temperature was 62° C. The mixture was heated at 80° C. for two hours after the addition was completed.

Volatiles were stripped from the reaction mixture and a mixture of 78.2g of water and 1 ml. of concentrated HCl were added. Stripping was then continued up to full aspirator vacuum. The residue was then vacuum distilled. The product was collected at 105°-118° C and 0.08-0.11mm (446g, 50% yield). The literature boiling point is 118° C. and 0.25mm. The infra red spectra showed a strong carbonyl absorption at 1712cm$^{-1}$ and a strong phosphoryl absorption at 1240cm$^{-1}$.

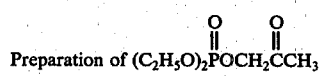

V.

To a one liter, three-neck flask equipped with a mechanical stirrer, reflux condenser and pot thermometer the following were added:
Dimethyl sulfoxide-450g
Diethylsodium phosphate-230g
Chloroacetone-160g (33% excess)

The mixture was stirred 1 hour at room temperature followed by 11 hours at 80° C. Gas chromatography indicates that the reaction has gone to completion. The product mix was vacuum distilled. Dimethyl sulfoxide distills over at 45°-65° C. at 0.15-0.5mm. The product was distilled at 101°-110° C. at 0.12 to 0.3mm. It appeared to be about 90% pure by gas chromatography. The yield is 142g or 53.8%. This preparation is very similar to that reported by K. Kraus, Compt. Rend. C271, 74 (1970).

B. Derivatives of Phosphorus Aldehydes & Ketones
  1. Hydrogen phosphonate adducts
    a. 1-[(diethyl) phosphono]-3-[(dimethyl) phosphono]-1-butanol;

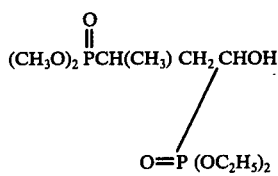

was prepared by mixing diethyl phosphite (61g) with triethylamine (1.0g) followed by addition of

over a 15 minute period. No exotherm was noted. The mixture was heated in a 250 ml single neck flask over a steam bath for 3 hours, i.e., until the carbonyl absorption of the aldehyde had disappeared. The mixture was cooled to room temperature and a 0.02mm vacuum applied. A cold trap was used to trap the triethylamine being stripped away (0.8g collected). The resultant product had an acid number of 2.2 and 19.1% phosphorus content (theory=19.4% phosphorus).

b. Synthesis of 2[(diethyl)phosphono]-4-[(dimethyl)-phosphono]-2-butanol

Diethyl hydrogen phosphonate (77gram) was dissolved in benzene (200ml). Small chunks of freshly cut sodium (0.10 grams total) were added and the mixture stripped under a nitrogen atmosphere until the sodium had all reacted into solution (about one hour). To this benzene solution dimethyl(3-oxo-1-butyl) phosphonate was added dropwise over a forty minute period. During the addition, the pot temperature rose to a maximum of 37° C. The mixture was then heated at 50°–55° C. for 2 hours. The product was finally passed through a wiped film evaporator at 0.05 mm and 90° C. The resultant product had an acid number of 2.8 and a phosphorus content of 19.5%; theory is 19.5% phosphorus.

2. Mannich condensation products

Synthesis of 1[(diethyl)phosphono]-1-(N,N-dihydroxyethylamino) 3-[(diethyl)phosphono]butane a. The following reaction was carried out as described below

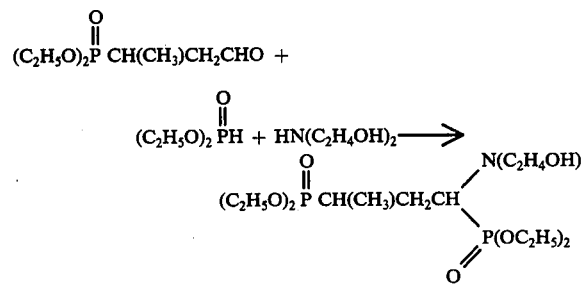

The diethyl hydrogen phosphonate (46.5g) and amine (35.4g) were mixed in a single neck 250ml flask. The aldehyde (70g) was then added in small portions (ca. 2ml) with stirring over a 20 minute period. A slight exotherm resulted. Fifteen minutes after the addition was complete, the carbonyl absorption in the infra red spectra had completely disappeared. The product was then stripped at 0.1 mm pressure and 50°–60° C. for 4 hours. The resultant product contained 14.5% phosphorus; theory is 14.8%.

b. An alternate procedure to the previous employing the same relative amounts of reagents was to mix the aldehyde and diethanol amine in toluene and azeotrope out the water formed. After water removal was complete, i.e., no more water forms in the collection vessel, the toluene was removed by vacuum stripping on a rotary evaporator under aspirator vacuum and a 50°–60° C. bath. To the residue, which contained little if any carbonyl absorption in the IR spectrum, the diethylhydrogen phosphonate was added. The mixture was stirred at room temperature for 18 hours and then at 60° C. for 8 hours. The infra red spectra of this product is essentially identical to that of the previous preparation with the exception of a slight amount of unreacted hydrogen phosphonate.

C. The following Mannich condensation was also carried out.

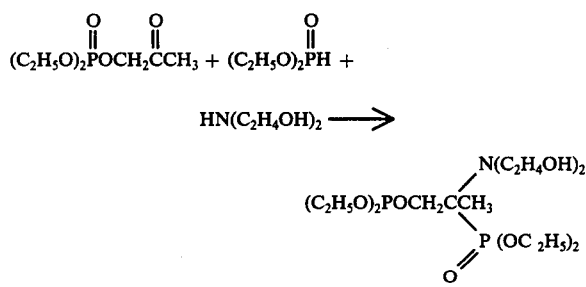

The diethanol amine (35g) and diethyl hydrogen phosphonate (46g) were mixed in a 250 ml flask equipped with a magnetic stirrer. The ketone (70g) was added to this mixture in small portions (ca.2ml) over a twenty minute period. The pot temperature rose to a maximum of 50° C. during the addition. Thirty minutes after the addition was complete the carbonyl and hydrogen phosphonate absorptions in the IR spectrum had essentially disappeared. The product at this point was too acidic (acid number greater than 32); therefore it was neutralized by the following procedure. The product was mixed with 100 ml of toluene and heated to 90° C.; dissolution was not complete. Twelve grams of propylene oxide was then added and the temperature kept at 90° C. for three hours. The mixture was then stripped under aspirator vacuum at 90° C. giving a neutral product containing 12.8 percent phosphorus.

C. Formaldehyde adducts of phosphorus aldehydes
Synthesis of 2- (dimethyl)phosphono -1,1,1, trimethylolpropane.

2-[(dimethyl) phosphono]butyraldehyde (96g) was dissolved in 300 ml of water. Then 40 g of paraformaldehyde was added followed by calcium oxide (40g) in small portions (ca. 1g). The temperature of the mixture rose to 50° C after about fifteen minutes; the calcium oxide addition was controlled so that the temperature remained at 50°–55° C. The mixture was stirred two hours after the final calcium oxide addition and then sulfuric acid (49g) was added in small portions. The resultant mixture was allowed to stand overnight. The supernatant liquid was decanted and the solvent vacuum stripped on a rotary evaporator. Methanol (250 ml) was added and then removed by vacuum rotary evaporator. This procedure was repeated two more times. The residual liquid was mixed with acetone (100 ml) to give a white amorphous solid weighing 80g after air drying. The product contained 13.1% phosphorus; theory is 12.7%.

D. Preparation of 3-[(dimethyl) phosphono]-1,1-bis(N,N-2-hydroxyethyl amino) butane 2-[(Dimethyl) phosphono]butyraldehyde (70g) was dissolved in benzene (140 ml) inside a 500 ml, 3-neck flask equipped with a Dean-Stark trap, thermometer, and magnetic stirrer. Diethanolamine (81.7g) was added slowly giving a slight exotherm to about 40° C. The mixture was then heated to 75°–80° C. and water was azeotroped from the reaction mixture. After 4 hours seven ml of water was collected. This is 100% of theory. The product mixture formed two layers on cooling. The lower layer was separated and stripped of volatiles at 0.3 mm and room temperature for 4 hours and then at 0.3 mm and 60° C for 6 hours. The final product contained 8.2% phosphorus; theory is 8.3%.

E. Preparation and Testing of Rigid Urethane Foams.

The following materials were weighed and mixed in the sequence given:

100 parts Poly G-435 — a propoxylated methyl glucoside tetrol with hydroxyl number 435 and molecular weight about 500

1.2 parts Surfactant-DC-193 from Dow Corning 1.2 parts amine catalyst-dimethylethanolamine 0.5 parts tin catalyst-Union Carbide D-22, dibutyltin dilaurate 50 parts freon-fluorotrichlormethane To the above well stirred mixture was added 114.2 parts of a polymeric isocyanate (PAPI, by Upjohn). This mixture was immediately mixed with a high-speed stirrer for 5–10 seconds and poured into a cardboard mold.

When the flame retardant was added it was mixed into the system just before the isocyanate.

Using this procedure several candidates were tested for their flame retarding ability. The flammability test used was the limiting oxygen index (LOI) in which a higher number implies better flame retardancy. The following results were found:

| Candidate | Loading | LOI |
|---|---|---|
| None | — | 20.0 |
| $(C_2H_5O)_2P(O)CH_2N(C_2H_4OH)_2$ (I) | 20 phr | 23.0 |
| I + $(BrCH_2BrHCCH_2O)_3PO$ (II) | 10 + 10 | 22.7 |
| $\underset{\underset{N(C_2H_4OH)_2}{\mid}}{(CH_3O)_2\overset{\overset{O}{\|}}{P}CH(CH_3)CH_2\overset{\overset{O}{\|}}{C}HP-(OCH_3)_2}$ | 20 | 22.9 |
| | 20 | 22.8 |
| $\underset{\underset{N(C_2H_4OH)_2}{\mid}}{(CH_3O)_2\overset{\overset{O}{\|}}{P}CH(CH_3)CH_2\overset{\overset{O}{\|}}{C}HP(O)(OC_2H_5)_2}$ | 20 | 23.0 |
| $\underset{\underset{N(C_2H_4OH)_2}{\mid}}{(CH_3O)_2\overset{\overset{O}{\|}}{P}CH_2CH_2\overset{\overset{O}{\|}}{C}(CH_3)P(OC_2H_5)_2}$ | 20 | 22.7 |
| $\underset{\underset{N(C_2H_4OH)_2}{\mid}}{(CH_3O)_2\overset{\overset{O}{\|}}{P}CH(CH_3)CH_2\overset{\overset{O}{\|}}{C}HP(OC_2H_5)_2}$ | 20 | 21.7 |
| $(CH_3O)_2P(O)CH(CH_3)C(CH_2OH)_3$ | 20 | 21.0 |
| $\underset{\underset{O=P(OC_2H_5)_2}{\mid}}{(CH_3O)_2\overset{\overset{O}{\|}}{P}CH(CH_3)CH_2CHOH}$ | 20 | 23.9 |

A further study was made employing two compositions as mixtures of constant phosphorus content with 10 phr of II above. The results are shown below.

| Candidate | Loading | %P.* | LOI |
|---|---|---|---|
| $(C_2H_5O)_2\overset{\overset{O}{\|}}{P}CH_2N(C_2H_4OH)_2$ | 20 phr | 12.2 | 23.4 |
| $\underset{\underset{O=P(OC_2H_5)_2}{\mid}}{(C_2H_5O)_2\overset{\overset{O}{\|}}{P}CH(CH_3)CH_2CH\ N(C_2H_4OH)_2}$ | 17.3 | 14.4 | 23.3 |
| $\underset{\underset{O=P(OC_2H_5)_2}{\mid}}{(C_2H_5O)_2\overset{\overset{O}{\|}}{P}CH(CH_3)CH_2CHOH}$ | 14.5 | 17.3 | 23.6 |

*%Phosphorus in the flame retardant.

These data indicate that the flame retardants with higher phosphorus content can be used in lesser amounts than flame retardants with lower phosphorus contents.

Having set forth the general nature and some examples of the present invention, the scope is now particularly set forth in the appended claims.

What is claimed is:

1. A flame retardant compound having the structure:

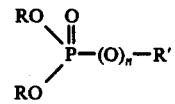

wherein $n$ is 0 or 1; $R'$ has a structure selected from the group consisting of

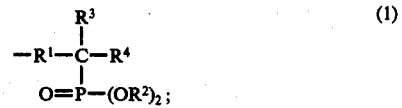
(1)

(2)

and

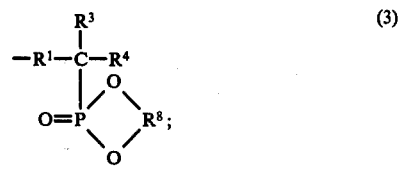
(3)

R and $R^2$ are the same or different and are selected from the group consisting of $C_1$-$C_6$ straight, branched and cyclic alkyl, aryl, aryl substituted $C_1$-$C_6$ alkyl, $C_1$-$C_6$ alkyl substituted aryl, and the hydroxylated derivatives thereof; $R^1$ is selected from the group consisting of straight and branched $C_1$-$C_6$ alkylene and $C_1$-$C_6$ alkenylene; $R^3$ is selected from the group consisting of hydrogen and $C_1$-$C_4$ straight and branched alkyl $R^4$ is selected from the group consisting of hydroxyl, and $-N(R^9)_2$ where $R^9$ is selected from the group consisting of $C_1$-$C_4$ alkyl and $C_1$-$C_4$ hydroxy alkyl; $R^5$ is selected from the group consisting of hydrogen and $C_1$-$C_6$ straight and branched alkyl; $R^6$ is selected from the group consisting of $-C(CH_2OH)_3$ and $-CH_2CH[N(R^9)_2]_2$ where $R^9$ is as defined above; and $R^7$ and $R^8$ are the same or different and are the difunctional analogs of R.

2. A flame retardant compound having the structure:

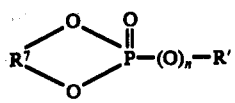

wherein $n$ is 0 or 1; $R'$ has a structure selected from the group consisting of

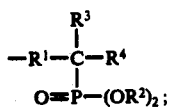 (1)

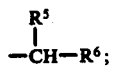 (2)

and

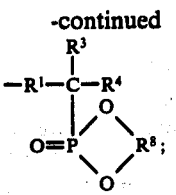 (3)

$R^2$ is selected from the group consisting of $C_1$-$C_6$ straight, branched and cyclic alkyl, aryl, aryl substituted $C_1$-$C_6$ alkyl, $C_1$-$C_6$ alkyl substituted aryl, and the hydroxylated derivatives thereof; $R^1$ is selected from the group consisting of straight and branched $C_1$-$C_6$ alkylene and $C_1$-$C_6$ alkenylene; $R^3$ is selected from the group consisting of hydrogen and $C_1$-$C_4$ straight and branched alkyl; $R^4$ is selected from the group consisting of hydroxyl, and —$N(R^9)_2$ where $R^9$ is selected from the group consisting of $C_1$-$C_4$ alkyl and $C_1$-$C_4$ hydroxy alkyl; $R^5$ is selected from the group consisting of hydrogen and $C_1$-$C_6$ straight and branched alkyl; $R^6$ is selected from the group consisting of —$C(CH_2OH)_3$ and —$CH_2CH[N(R^9)_2]_2$ where $R^9$ is as defined above; and $R^7$ and $R^8$ are the same or different and are the difunctional analogs of $R^2$.

* * * * *